United States Patent [19]

Yotsuya

[11] Patent Number: 4,953,100
[45] Date of Patent: Aug. 28, 1990

[54] APPARATUS FOR INSPECTING PACKAGED ELECTRONIC DEVICE

[75] Inventor: Teruhisa Yotsuya, Kyoto, Japan

[73] Assignee: Omron Tateisi Electronics Co., Kyoto, Japan

[21] Appl. No.: 104,149

[22] Filed: Oct. 5, 1987

[30] Foreign Application Priority Data

Oct. 3, 1986 [JP] Japan ................. 61-236499
Oct. 30, 1986 [JP] Japan ................. 61-256994
Oct. 30, 1986 [JP] Japan ................. 61-256995

[51] Int. Cl.$^5$ .................................. G06F 15/46
[52] U.S. Cl. ........................ 364/559; 356/394; 358/106; 371/25.1; 382/8
[58] Field of Search ......... 364/507, 514, 516, 551, 364/551.01, 552, 559; 358/106, 107, 108; 356/372, 375, 394; 371/25; 382/8, 26

[56] References Cited

U.S. PATENT DOCUMENTS

| | | | |
|---|---|---|---|
| 4,379,308 | 4/1983 | Kosmowski et al. | 358/106 |
| 4,433,385 | 2/1984 | De Gasperi et al. | 364/507 |
| 4,473,842 | 9/1984 | Suzuki et al. | 358/106 X |
| 4,486,777 | 12/1984 | Yamamura | 364/507 |
| 4,589,139 | 5/1986 | Hada et al. | 358/107 X |
| 4,644,584 | 2/1987 | Nagashima et al. | 382/8 X |
| 4,656,510 | 4/1987 | Mattila | 358/107 |
| 4,692,943 | 9/1987 | Pietzsch et al. | 382/8 |
| 4,700,225 | 10/1987 | Hara et al. | 382/8 |
| 4,707,734 | 11/1987 | Labinger et al. | 356/106 |
| 4,758,782 | 7/1988 | Kobayashi | 382/8 |
| 4,760,444 | 7/1988 | Nielson et al. | 364/552 |
| 4,764,969 | 8/1988 | Ohtombe et al. | 358/107 |
| 4,794,647 | 12/1988 | Forgues et al. | 358/106 X |
| 4,799,175 | 1/1989 | Sano et al. | 358/106 X |
| 4,876,656 | 10/1989 | Leicht et al. | 364/559 X |

OTHER PUBLICATIONS

"Testing System for Manufactured Circuit Cards", IBM Technical Disclosure Bulletin, vol. 22, #6, Nov. 1979, pp. 2221-2222.

Primary Examiner—Parshotam S. Lall
Assistant Examiner—Edward R. Cosimano
Attorney, Agent, or Firm—Wegner & Bretschneider

[57] ABSTRACT

A component-mounted printed circuit board inspecting apparatus comprises an imaging device for picking up images of printed circuit board. Land images are extracted from the image of a bare printed circuit board and that of a component-mounted printed circuit board. On the basis of the shapes of the land extracted from the bare printed circuit board and those of the component-mounted printed circuit board, the positional relationship between a comonent mounted on the printed circuit board and the land thereon is determined. This positional relationship is utilized to decide if the component is mounted properly on the printed circuit board.

5 Claims, 14 Drawing Sheets

FIG.18
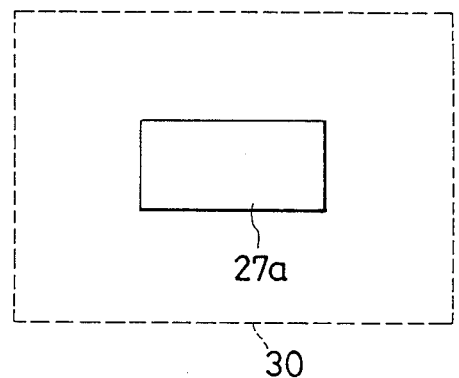
FIG.19(A)    FIG.19(B)
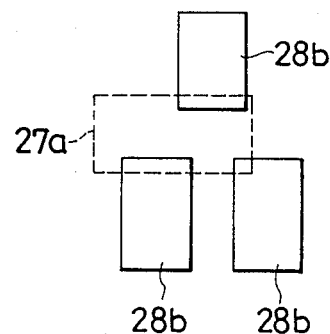 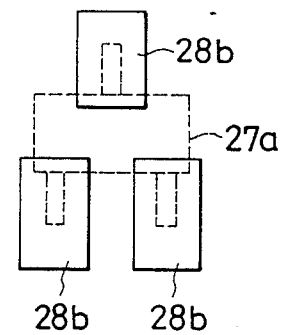
FIG.20(A)    FIG.20(B)
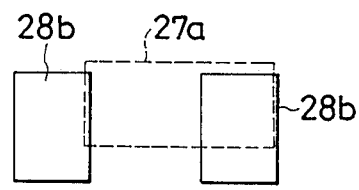 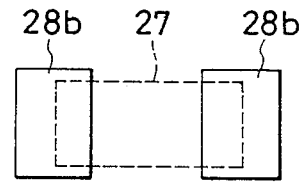

APPARATUS FOR INSPECTING PACKAGED ELECTRONIC DEVICE

BACKGROUND OF THE INVENTION

1. Field of the Invention

The present invention relates to an apparatus for inspecting component-mounted electronic devices. More particularly, the invention relates to an apparatus for inspecting a printed circuit board (hereinafter referred to as a "substrate") mounted or equipped with electronic components (hereinafter referred to as "packaged"), the apparatus being capable of automatically discriminating between the types of species of the components and determining whether the components are mounted in the correct positions on the substrate.

2. Description of the Prior Art

As the packaged substrate inspecting apparatus (also known as the package inspecting system) for inspecting the packaged electronic/electric device equipped with electric and/or electronic parts by means of a mounter or the like apparatus, there has been heretofore known such a structure as shown schematically in FIG. 1 of the accompanying drawings.

As will be seen in this figure, the packaged substrate inspecting apparatus or system is composed of a television camera (referred to simply as TV camera) 3 for picking up an image (also referreed to as imaging) of a substrate 2b on which electronic/electric parts are mounted or packaged and which is to be inspected and a reference packaged substrate 2a (which serves as a reference or standard substrate) for inspection, a memory 4 unit in which the image (reference image) of the reference packaged substrate 2a picked by the TV imaging camera 3, a comparison/decision circuit 5 for comparing the data of image (image to be examined) of the packaged substrate 2b under inspection available from the TV camera 3 with the reference image data read out from the memory 4 for making decision as to whether all requisite parts 1b are mounted on the packaged substrate 2b under test or whether any of the mounted parts are displaced or dislocated from the respective correct positions, and a display unit 6 for displaying the results of the decision issued by the comparison/decision circuit 5.

The prior art packaged substrate inspecting apparatus of the type outlined above is so designed as to compare simply the position of the part 1a mounted on the standard or reference packaged substrate 2a with that of the part 1b mounted on the printed substrate under inspection, wherein upon detection of positional incoincidence between these parts 1a and 1b, it is determined that the part 1b is not mounted correctly. In this way, the decision of failure in mounting of the part is always issued whenever the part mounted on the packaged substrate 2b under test is dislocated from the standard or correct position 7 (the position indicated by the part 1a on the standard substrate 2a), as is illustrated in FIG. 2 of the accompanying drawings, even if the part 1b on the substrate 2b under test is so positioned that electrodes thereof can be electrically connected to the respective mounting lands 9b, as is shown in FIG. 3.

In order to evade the inconvenience mentioned above, it is conceivable that a permissible range 8 within which the part 1b mounted on the substrate is allowed to be positionally deviated more or less is previously established on the basis of the correct or standard position of the part 1b, wherein so far as the part 1b is found to be located within the permissible range, it is decided that the part 1b is mounted correctly. In that case, however, the permissible range 8 has to be prepared for each part 1b in dependence on the species thereof, because the geometrical factor such as profile or outline of the permissible range 8 will vary from one to another part. By way of example, the dimension as well as geometry of the permissible range 8 for a transistor having three electrodes will differ from that for a resistor or capacitor having two electrodes. Consequently, very troublesome and time consuming procedure will be involved in preparing and registering a great variety of data concerning the permissible ranges 8 of various sizes and profiles in the inspection system.

Besides, experience shows that the circuit pattern printed on the substrate slightly differ from one to another even though a same patterning mask is employed. Consequently, even when the part 1b is correctly mounted relative to the land 9 of the substrate 2a, there arises a possibility that decision of failure in mounting will be issued when the position of the land 9 on the substrate 2a under test differs from that of the corresponding land on the standard substrate 2a, i.e. when the land position 9a and the part position 10a on the standard substrate 2a of which data have been previously loaded in the memory unit 4 are deviated from the land position 9b and the part position 10b obtained by imaging the packaged substrate 2b under test with the TV camera 3, as illustrated in FIG. 3, notwithstanding of the fact that the part position 10b actually lies in a correct positional relationship with the land position 9b, giving rise to another problem.

SUMMARY OF THE INVENTION

In view of the difficulties of the prior art package inspection system described above, it is therefore a first object of the present invention to provide a packaged substrate inspecting apparatus which is capable of automatically setting or establish the permissible ranges of positional deviation or dislocation for the individual electric/electronic parts and which is so arranged as to decide that a part is mounted satisfactorily so far as that part is located within the permissible range on the associated land even when the land position differs from one to another packaged substrate to be inspected, to thereby exclude the erroneous decision ascribable to manufacturing tolerance of the substrate, and which apparatus is additionally so implemented as to be capable of recognizing geometrical configuration of those portions of the substrate under inspection which are hidden by the parts formed or mounted thereon.

It is a second object of the present invention to provide a packaged substrate inspecting apparatus which is capable of automatically detecting selectively and extractively the land formed on the substrate to thereby inhibit erroneous or falsified decision attributable to manufacturing tolerance of the substrate and additionally capable of recognizing the geometrical configuration of those portions of the substrate under test which are hidden by the parts mounted thereon.

A third object of the present invention is to provide a packaged substrate inspecting apparatus which can automatically identify the types or species of the parts discriminatively to thereby establish automatically the permissible range or margin of positional deviations which are appropriate or proper to the individual parts, respectively.

For accomplishing the above and other objects which will be more apparent as description proceeds, there is provided according to an aspect of the present invention a packaged substrate inspecting apparatus which comprises land extracting means for extracting lands from images of a non-packaged substrate and a packaged substrate, respectively, produced by image pick-up means, positional relation extracting means for extracting the positional relationship between the lands of the packaged substrate and parts mounted thereon on the basis of data of geometrical land configurations of the non-packaged substrate and the packaged substrate, which data are obtained by the land extracting means, and decision means for deciding the mounted state of the part on the basis of the positional relationship of which data supplied from the positional relationship extracting means.

According to another aspect of the present invention, there is provided a packaged substrate inspecting apparatus which comprises imaging means for picking up images of substrates, image cut-out means for cutting out a plausible land existing range from the image obtained by the imaging means on the basis of previously inputted data concerning the positions and geometrical configurations of parts, land extracting means for extracting the land from the cut out image produced by the image cut-out means, and decision means for determining the type or speciesof the parts on the basis of the land data available from the land extracting means and the previously inputted data concerning the positions and geometrical configurations of the parts.

According to a further aspect of the present invention, the packaged substrate inspecting apparatus comprises imaging means for picking up color image of a substrate, hue value converting means for performing hue value conversion of individual pixels (picture elements) of the substrate image produced by the imaging means, and decision means for deciding that the pixel whose hue value in red outputed by the conversion means exceeds a predetermined value is that of a copper foil.

With the aforementioned arrangements of the inspection system according to the invention, the range of the permissible positional deviation can be automatically and optimally established appropriately to individual parts mounted on a substrate. Even in the case the land on the packaged substrate under inspection differs from one to another substrate, decision of satisfactory mounted state of a part can be made so far as the part of concern is mounted within the permissible range on the land, whereby falsified or erroneous decision which might otherwise be brought about due to manufacturing tolerance of the substrate can be positively prevented. Besides, the shapes of those portions of the substrate under inspection which are hidden by parts formed or mounted thereon can be detected for recognition.

Additionally, the species or types of the individual parts mounted on the substrate can be discriminatively identified in an automated manner, whereby the permissible positional deviation margin optimally appropriate to the parts can be established.

Further, since the lands formed on the substrate can be automatically extracted, erroneous decision due to manufacturing tolerance of the substrate can be inhibited. In addition, the shapes or profiles and other parameters of those portions of the substrate under inspection are hidden by the parts mounted thereon can be detected.

The above and other objects, novel features and advantages of the present invention can be fully understood upon consideration of the following detailed descrption of the illustrative embodiments presented only by way of example and taken in conjunction with the accompanying drawings.

BRIEF DESCRIPTION OF THE DRAWINGS

FIG. 18 is a view showing, by way of example, a plausible land existing range which is made use of in the part identifying procedure shown in FIG. 17;

FIG. 19A is a view showing an image pattern which allows a part of concern mounted on a substrate to be identified as a transistor;

FIG. 19B is a view for illustrating the mounted position correcting operation for the transistor shown in FIG. 19A;

FIG. 20A is a view showing an image pattern which allows the part of concern mounted on the substrate to be identified as a resistor or a capacitor;

FIG. 20B is a view for illustrating the mounted position correcting operation for the part showing in FIG. 20A;

DESCRIPTION OF THE PREFERRED EMBODIMENTS

Figure 1:
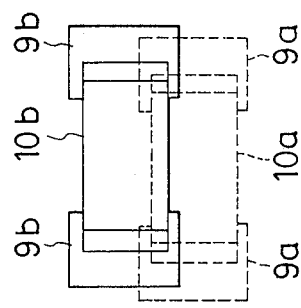
FIG. 1 is a view showing schematically in a block diagram an exemplary arrangement of a hitherto known packaged substrate inspecting apparatus.
Figure 3:
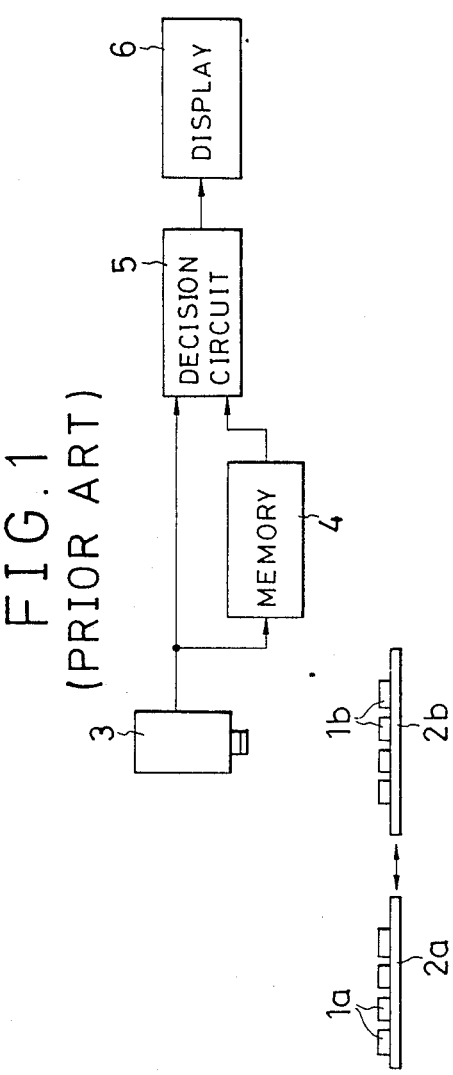
FIG. 3 is a schematic diagram for illustrating a positional relationship between parts to be mounted on a substrate and mounting lands formed thereon.
Figure 2:
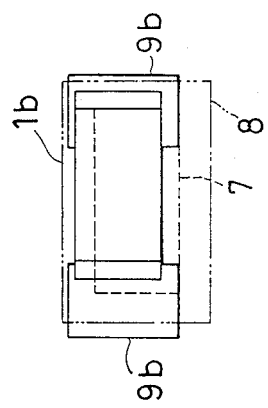
FIG. 2 is a schematic diagram for illustrating positional deviation or dislocation of parts mounted on a substrate as detected by the prior art package inspecting apparatus.

Now, the present invention will be described in detail in conjunction with the preferred embodiments illustrated in the drawings.

Figure 4:
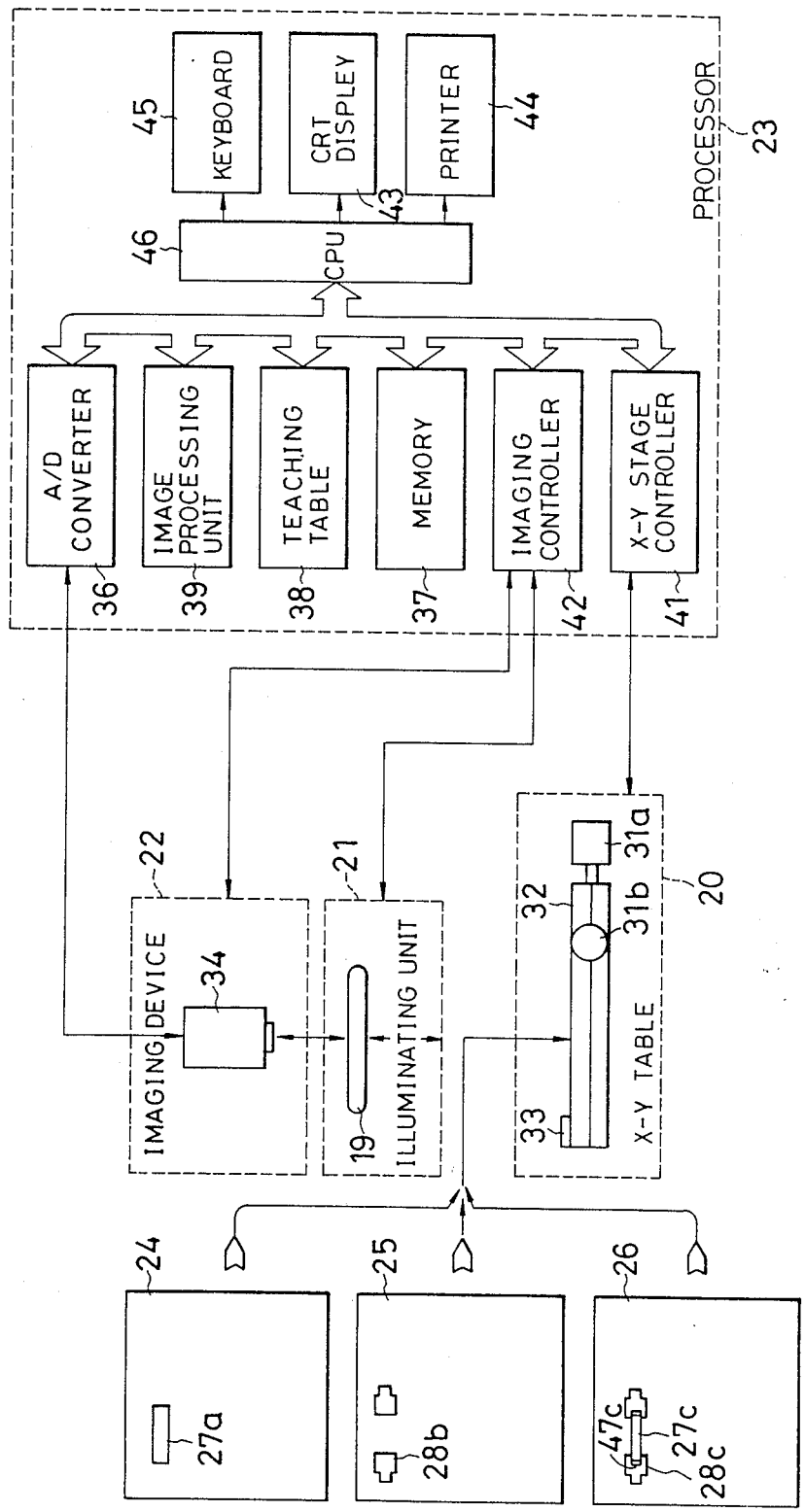
FIG. 4 is a view showing in a block diagram a general arrangement of a packaged electronic device or packaged substrate inspecting apparatus according to an exemplary embodiment of the invention.

FIG. 4 is a view showing in a block diagram a general arrangement of a packaged substrate inspecting apparatus or system according to an exemplary embodiment of the invention.

Referring to the figure, the packaged substrate inspecting apparatus includes an X-Y table or stage unit 20, an illuminating unit 21, an image pick-up device 22, and a processing unit generally denoted by a numeral 23. The principle underlying the instant embodiment resides in that a plausible land existing region or range is arithmetically determined on the basis of the data concerning a land 28b derived from processing of the picked-up image of a non-packaged substrate 25, wherein the plausible land existing region or range which may also be referred to as the permissible land region or range is of a greater area than the land 28b. With the aid of data of the permissible land region or plausible land existing range, an image portion covering a head 28c actually existing on the packaged substrate 26 under inspection is cut out, being followed by extraction of the land 28c from the cut-out image portion mentioned above. Through comparison of the lands 28b with 28c in respect to the geometrical configuration, the portion of the land 28c on the packaged substrate under inspection which is hidden by a part 27c mounted thereon can be determined. On the basis of the information of the hidden portion, the positional relationship between the land and the part 27c is determined to thereby decide whether the part 27c is mounted correctly or not.

The illuminating unit 21 includes a ring-like white light source 19 which is turned on and off (or intensity-controlled) by a control signal supplied from the aforementioned processing unit 23. More specifically, when an illumination activating signal is supplied from the processing unit 23, the later is lit to illuminate continuously the top surface of the X-Y table 20 until an illumination deactivating signal is supplied from the processing unit 23.

The X-Y table (stage) assembly 20 includes pulse motors 31a and 31b operated in response to control signals supplied from the processing unit 23, a X-Y table adapted to be driven in the X- and Y-directions by the pulse motors 31a and 31b, respectively, and a chuck mechanism 33 provided in combination with the X-Y table 32 for securing fixedly the substrates 24, 25 and 26 on the table 32 in response to a control signal which is produced by the processing unit 23 when the substrates 24, 25 and/or 26 is positioned on the X-Y table 32. Images of the substrates 24, 25 and 26 secured by the chuck mechanism 33 are picked up by the image pick-up device 22 under illumination by the illuminating unit 21.

The image pick-up device or imaging device 22 is equipped with a color TV (television) camera 34 disposed above the illumination unit 21, whereby the optical images of the substrates 24, 25 and 26 are converted into electric image signals (i.e. video signals) containing color or chrominance components R (red), G (green) and B (blue), the video signals thus produced are supplied to the processing unit 23.

The processing unit 23 includes an analogue-to-digital (A/D) converter 36, a memory 37, a teaching table storage 38, an image processor unit 39, a X-Y table or stage controller 41, an imaging controller 42, a CRT (cathode ray tube) display 43, a printer 44, a keyboard 45, and a central processing unit (hereinafter referred to as CPU) 46.

In the teaching mode, the color or chrominance signal components R, G and B supplied from the image pick-up device 22 and reflecting the colors of the substrates 24 and 25 are processed to create an inspection data file to be referenced upon inspection of a packaged substrate 26 under test. At the time of inspection or examination of the packaged substrate 26, the chrominance component signals R, G and B supplied from the image pick-up device 22 for picking up the image of the packaged substrate 26 under inspection are processed by reference to the aforementioned inspection file, wherein the result of the processing is utilized in deciding whether the relative position between the part 27c and the land 28c formed on the packaged substrate under test lies within a permissible range or not. The result of the decision is indicated on the CRT display 43.

The A/D converter 36 is supplied with image or video signal (chrominance signal components R, G and B) from the aforementioned imaging device 22 for creating color image data through analogue-to-digital conversion, the resultant image data being then supplied to the CPU 46.

The memory unit 37 includes a random access memory or RAM or the like which serves as the work area for the CPU 46.

The image processor 39 is supplied with the image data by way of the CPU 46 for digitizing the data and is arranged as to extract the position and shape (profile) data of electric/electronic parts, cut out relevant image portions from the image data, perform hue value conversion, transform the result of the hue value conversion into a binary signal with reference to a preset threshold value for extracting the data of position, geometrical configuration (shape) or other factors of the land pattern. All the data generated by the image processor 39 are supplied to the CPU 46.

The teaching table storage 38 includes a floppy disc device for storing therein data file for inspection or other purposes supplied from the CPU 46. When a transfer request is issued from the CPU 46, the inspection data file is read out to be subsequently transferred to the CPU 46.

The imaging controller 42 is provided with an interface for connection to the CPU 46, illuminating unit 31 and the image pick up device 22 for controlling the illuminating unit 21 and the image pick-up device 22 in accordance with the command signals issued by the CPU 46.

The X-Y stage controller 41 includes an interface for connection to the CPU 46 as well as to the X-Y table assembly 20 for controlling the latter in accordance with the command signal outputted from the CPU 46.

The CRT display unit 43 includes a cathode ray tube (CRT) for display on the screen thereof the image data and the results of decisions made by the CPU 46 as well as data inputted through a keyboard 45.

The printer 44 is adapted to print out the results of decision supplied from the CPU 46 in a predetermined format.

The keyboard 45 includes a variety of keys required for inputting the data or information required for operation of the system, the names and sizes of packaged electronic/electric devices or substrates 26 to be inspected as well as data concerning the parts 27c mounted on the substrate 26. The data and information entered through the keyboard 45 are supplied to the CPU 46.

The CPU or central processing unit 46 is constituted by a microprocessor and other associated circuits and adapted to perform operations described below.

Figure 5:
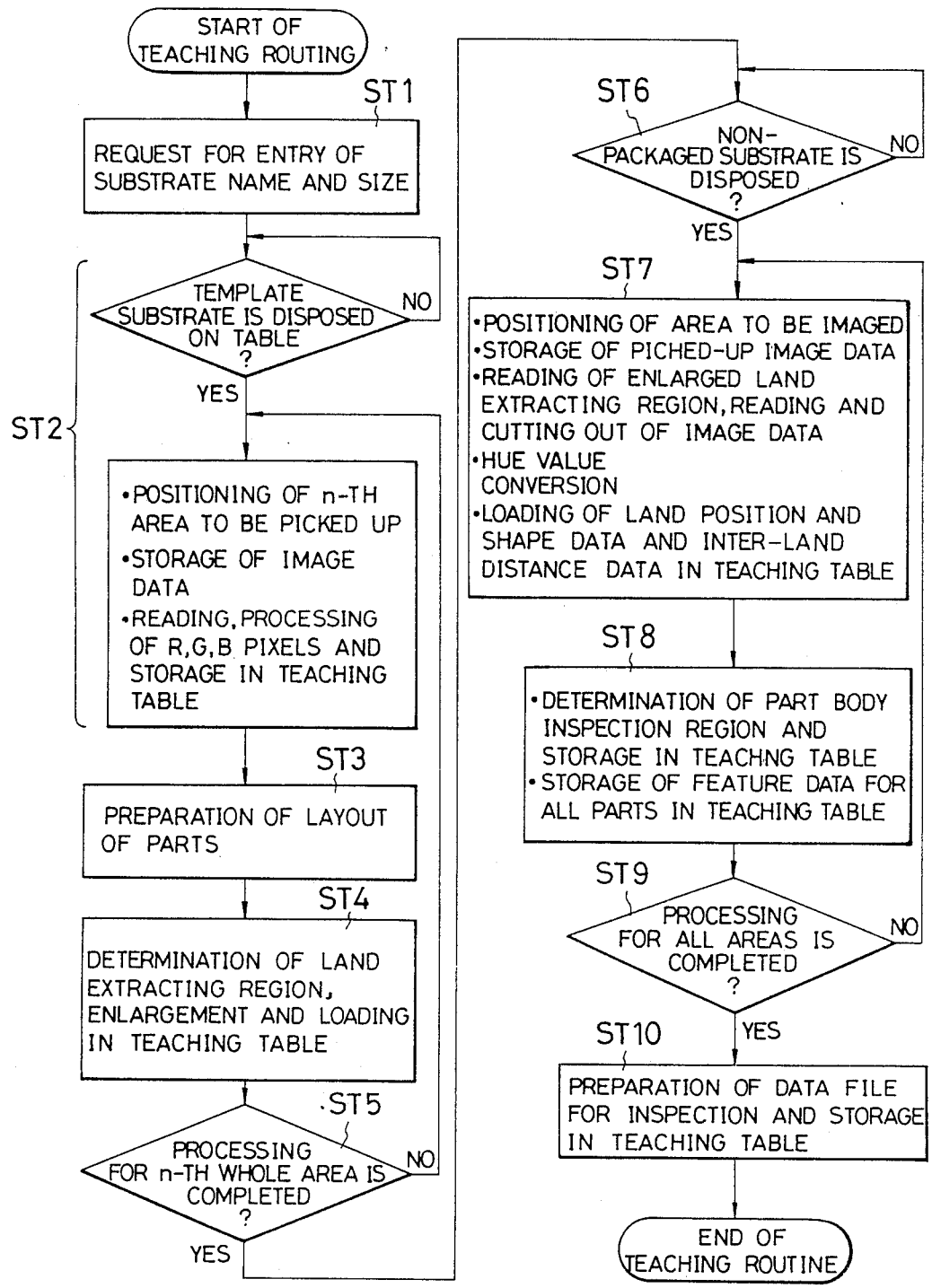
FIG. 5 is a view illustrating in a flow chart a teaching routine for teaching a procedure for determining mounted states of parts on a substrate in the packaged substrate inspecting apparatus shown in FIG. 4.

When a new packaged substrate 26 is to be inspected, the CPU 46 commands the CRT display unit 43 to display a message requesting for the entry of data concerning the identification name (e.g. identification number) of the substrate to be inspected and the size thereof, as illustrated in a teaching flow chart of FIG. 5 at a step ST1.

When the substrate identification and size data as prompted on the CRT display 43 are entered through the keyboard 45, the CPU 46 waits for disposition of a template substrate designed for use in executing the teaching procedure on the X-Y table or stage 32 at a step ST2. In this connection, it should be mentioned that the template substrate is colored in white at regions where electric/electronic parts are to be mounted with the remaining area being painted in black. When the template substrate 24 has been disposed on the X-Y table assembly 20, the CPU 46 causes the table assembly 20 to be moved through the X-Y stage controller 41 so that a first area of the template substrate 24 whose image is to be picked up is positioned below the color TV camera 34.

The image information produced by the color TV camera 34 undergoes A/D conversion through the A/D converter 36 under the control of the CPU 46.

The results of the A/D conversion (i.e. the digitized image data of the substrate 24) is stored in the memory 37 on the real time basis.

Subsequently, the CPU 46 reads out successively the image data of R-pixels (or alternatively, G- or B-pixels) from the memory 37. The image data as read out are then converted into binary signals through the image processor 39, from which the data concerning the white regions on the substrate 24 (the part portion 27a) is extracted. Subsequently, positional data as well as shape (profile) data of the parts 27a obtained through the extracting operation are loaded in the teaching table 38.

Figure 7:
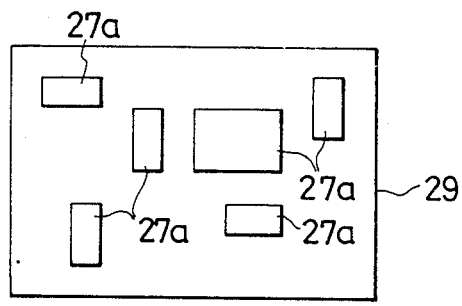
FIG. 7 is a view showing schematically an example of positions and geometrical configurations displayed on a display unit incorporated in the packaged substrate inspecting apparatus shown in FIG. 4.

At a step ST3, the CPU 46 creates a layout image 29 of the parts on the basis of the position data and the shape or profile data of the parts 27a, the layout image being then displayed on the CRT display unit 43, as is shown in FIG. 7. For a specific part, the CPU 46 can produce a message prompting the operator to input manually the relevant data through the keyboard 45.

When the position data and the profile or shape data are entered by the operator for the specific parts, the associated position data and shape data stored in the teaching table 38 is modified correspondingly.

Subsequently, at a step ST4, the CPU 46 generates a message on the CRT display 43 prompting the operator to enter information concerning the type or species of the individual parts 27a as well as orientations in which the parts 27a are to be mounted on the substrate. When the information as requested is loaded by the operator, the regions in which the mounting lands are positioned (referred to as the land extracting regions) are determined on the basis of the data concerning the shape, species and the orientation of the individual parts.

Figure 8:
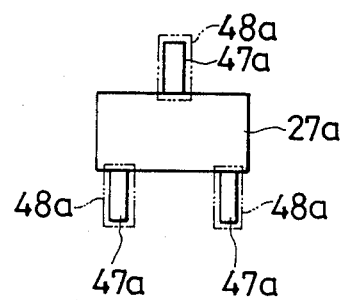
FIG. 8 is a schematic view for illustrating extraction of mounting lands for a transistor or the like part.
Figure 9:
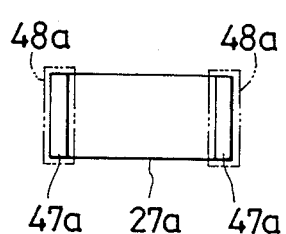
FIG. 9 is a schematic view for illustrating extraction of mounting lands for a resistor, a capacitor or the like part.

In this connection, it is assumed that the part 27a is a triplet-electrode part such as a transistor. In that case, the land extracting regions 48a which cover electrodes 27a of the part 47, respectively, and which extend outwardly therefrom is determined, as is illustrated in FIG. 8. On the other hand, in case the part 27a is a double-electrode part such as a resistor, a capacitor or the like, such land extracting regions 48a are prepared which cover the electrodes 47a formed at both ends of the part, respectively, and extend outwardly thereof, as is illustrated in FIG. 9.

Figure 10A:
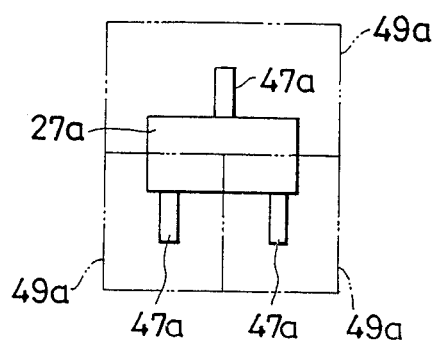
FIG. 10A is a schematic view showing an enlarged land extracting region for a transistor or the like part.
Figure 10B:
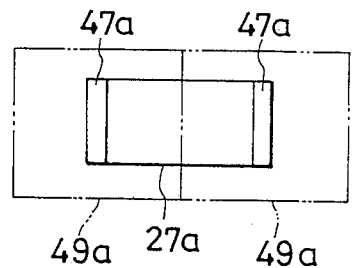
FIG. 10B is a schematic view showing an enlarged land extracting region for a resistor, a capacitor of the like part.

Subsequently, the land extracting regions 48a are enlarged, respectively, to create enlarged extracting regions 49a, as illustrated in FIGS. 10A and 10B for both of the assumed cases mentioned above. The data of the enlarged land extracting regions are then stored in the teaching table storage 38.

Thereafter, the abovementioned processing is executed for other parts to be mounted in the first picked-up area (i.e. n=1 at the step ST2).

When the processing for preparing the land extracting regions 49a for all the parts 27a to be disposed within the first area has been completed, the routine returns to the step ST2 by way of a step ST5, being followed by repeated execution of the abovementioned processing for all of the remaining picked-up areas. When the requisite data of the land extracting regions 49 for all the parts 27 belonging to every picked-up area have been obtained, the teaching routine makes a jump to a step ST6 from the step ST5.

At the step ST6, the CPU 46 waits for the positioning of a non-packaged substrate 25 on the X-Y table or stage 20 after the template substrate for the teaching purpose is removed.

When the non-packaged substrate 25 is positioned on the X-Y table 20, then the step ST7 is executed. At this step, the CPU 46 causes the X-Y table assembly 20 to be moved through the X-Y stage controller 41 so that a first area of the non-packaged substrate 25 whose image is to be picked is positioned beneath the color TV camera 34.

Subsequently, the image signal generated by the color TV camera 34 is subjected to A/D conversion under the control of the CPU 46, the result of which (i.e. image data of the non-packaged substrate 25) are stored in the memory 37 on the real time basis.

Next, the CPU 46 reads out the data of the enlarged land extracting regions 49a from the teaching table 38 and supplies the data to the image processor unit 39 which is also supplied with the image data of the non-packaged substrate 25 read out from the memory 37. In the image processor unit 39, an image (referred to as intra-land image) is cut out from the data of each land extracting region 49a.

Subsequently, the CPU 46 issues a hue value conversion command to the image processor unit 39 which responds thereto by performing the hue value conversion on pixels constituting parts of the intra-land image in accordance with hue value conversion equations, exemplified by the following:

$$BRT(i,j) = R(i,j) + G(i,j) + B(i,j) \quad (1)$$

$$Rc(i,j) = \alpha \cdot R(i,j)/BRT(i,j) \quad (2)$$

$$Gc(i,j) = \alpha \cdot G(i,j)/BRT(i,j) \quad (3)$$

$$Bc(i,j) = \alpha \cdot B(i,j)/BRT(i,j) \quad (4)$$

where

R (i, j) represents the intensity of R-signal component of the pixel (i, j) located at an intersection of the i-th row and the j-th column, G (i, j) represents the intensity of G-signal component of the pixel (i, j) located at an intersection of the i-th row and the j-th column, B (i, j) represents the intensity of B signal component of the pixel (i, j) located at an intersection of the i-th row and the ij-th column, BRT (i, j) represents the brightness of the pixel (i, j), α represents a coefficient, Rc (i, j) represents red hue value of the pixel (i, j), Gc (i, j) represents green hue value of the pixel (i, j), Bc (i, j) represents blue hue value of the pixel (i, j).

Upon completion of the abovementioned hue value conversion for all the pixels within the land extracting region 49a, the CPU 46 checks whether the red hue values Rc (i, j) of all the pixels (i, j) within the land extracting region 49a exceed a land extracting reference value C (e.g. C=0.4·α) which has been previously loaded, for thereby extracting the land 28b located within the land extracting region 49a.

Subsequently, the position data as well as shape or profile data of the land 28b is stored in the teaching table 38 under the command of the CPU 46. At the same time, the CPU 46 arithmetically determines the inter-land distance among the lands destined for mounting the individual parts 27a, respectively, the results of which are also stored in the teaching table 38 in the form of the distance data.

It should be mentioned that the distance data are utilized for indicating the permissible tolerances involved in mounting the parts to a mounter (a part mounting mechanism) or for evaluating the land pattern.

Figure 11A:
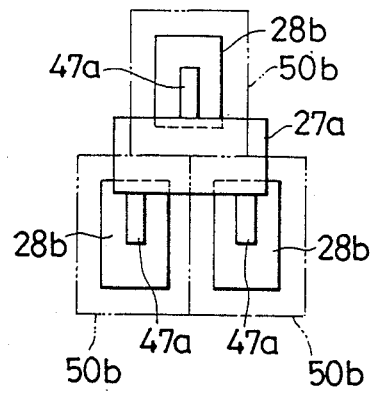
FIG. 11A is a schematic view showing an enlarged land inspecting region of a transistor or the like part.
Figure 11B:
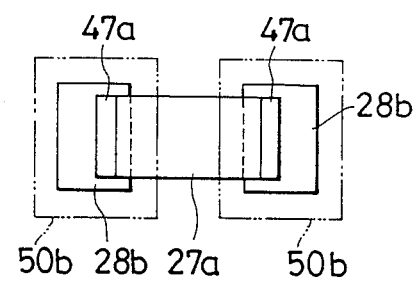
FIG. 11B is a schematic view showing an enlarged land inspecting region of a resistor, a capacitor or the like part.

Next, the CPU 46 expands or enlarges the shape (profile) data of the land 28b, as is illustrated in FIGS. 11A and 11B, to arithmetically determine the land inspecting region 50b, the resulting data of the land inspecting region being stored in the teaching table 38.

Figure 12A:
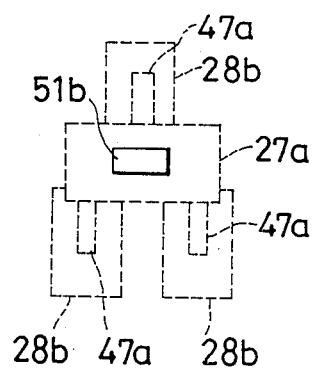
FIG. 12A is a schematic view showing a part body inspecting region for a transistor or the like part.
Figure 12B:
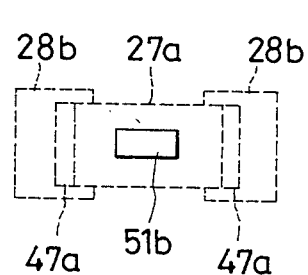
FIG. 12B is a schematic view showing a part body inspecting region for a resistor, a capacitor or the like part.

Thereafter, at a step ST8, the CPU 46 arithmetically determines a part body inspecting region 51b for cutting out the image of a center portion of each part 27a on the basis of the data concerning the position and shape (profile) of the land, as illustrated in FIGS. 12A and 12B, the results being also stored in the teaching table 38. At this stage, a message requesting the feature data (e.g. color data) of the body of each part 27a is displayed on the CRT display unit. In response, operator enters all the feature data for all the parts 27a manually through the keyboard 45, which are then stored in the teaching table 38.

The abovementioned processing is repeatedly executed for all the remaining parts 27a within the first picked-up area.

Upon completed execution of the routine including the land extraction processing to the feature data load processing for all the parts 27a within the first picked-up area, the CPU 46 returns to the step ST6 by way of the step ST9, whereupon the processing described above is repeatedly performed for all the remaining areas picked-up by the imaging device 3.

When the aforementioned processing comes to an end after having been performed for all the parts located in all the picked-up image areas, the program executed by the CPU 46 goes to a step ST10 from the step ST9.

At the step ST10, the CPU 46 rearranges the data stored in the teaching table 38 to prepare an inspection data file which is again stored in the teaching table 38, whereupon the teaching operation comes to an end.

Figure 6:
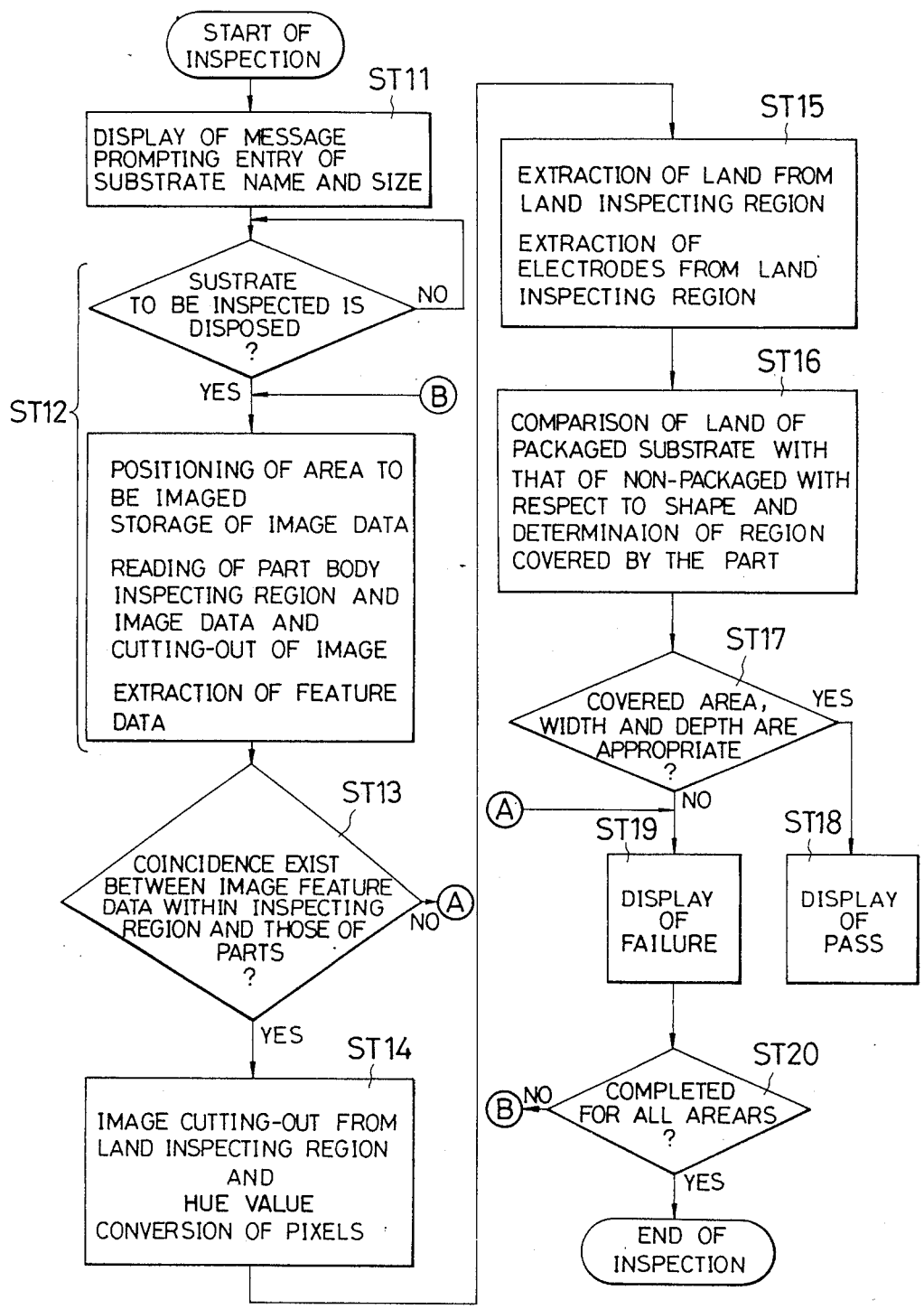
FIG. 6 is a view illustrating in a flow chart a procedure executed for inspecting the mounted state of parts on a substrate by the pachaged substrate inspecting apparatus shown in FIG. 4.

When an inspection mode is activated at the end of the teaching operation, the CPU 14 generates a message on the screen of the CRT display unit 43, the message requesting the loading of identification name of a packaged substrate 26 to be inspected at a step ST11 shown in the inspection flow chart illustrated in FIG. 6.

After the identification name of the substrate has been entered by operator through the keyboard 45, the CPU 46 waits for disposition of a corresponding packaged substrate 26 to be inspected on the X-Y table 32 at a step ST12. When the substrate 26 to be inspected is disposed, the CPU 46 causes the X-Y table 32 to be moved through the X-Y stage controller 41 to the position where the first area to be imaged of the packaged substrate 26 for inspection is located below the color TV camera 34.

The image signal produced by the color TV camera 34 is converted into a digital signal through the A/D converter 36 under the control of the CPU 46, the result of the A/D conversion (i.e. image data of the packaged substrate 26 under test) are stored in the memory 37 on the real time basis.

Subsequently, the CPU 46 reads out the data of a part body inspection region 51b from the teaching table 38 and supplies them to the image processor unit 39 which is also supplied with the image data of the packaged substrate 26 from the memory 37. In the image processor unit 39, the image of the region 51b to be inspected is cut out from the image data.

Next, the CPU 46 issues a feature extracting command to the image processor unit 39 which responds thereto by extracting the feature data of the image of the cut-out inspection region 51b (which can be accomplished, for example, through hue value conversion of pixels of the image).

Thereafter, the CPU 46 makes decision at a step ST13 as to whether the feature data of the image within the aforementioned inspection region 51b coincides with the feature data of the parts 27a stored in the teaching table 38. If coincidence is found, the inspection routine makes a jump from the step ST13 to a step ST14 where the land inspection region 50b is read out from the teaching table 38 and transferred to the image processor unit 39 which is also supplied with the image data of the packaged substrate 26 under inspection from the memory 37, whereupon the image of the land inspection region 50b is cut out from that image data.

At this stage, the CPU 46 issues a command for hue value conversion to the image processor unit 39, whereby the individual pixels (picture elements) constituting the aforementioned land inspection region 50b undergo the hue value conversion.

Upon completion of the hue value conversion mentioned above for all the pixels within the land inspection region 50b, the CPU 46 checks whether the red hue value Rc (i, j) for each pixel within the land inspection region 50b exceeds a preset land extraction reference value C (e.g. C may be selected equal to $0.4 \cdot \alpha$), to thereby extract the land 28c located within the land inspection region 50b at a step ST15.

Subsequently, the CPU 46 checks whether the brightness BRT (i, j) of each pixel within the land inspection region 50b exceeds a preset reference value D for extraction of electrodes, to thereby extracts the electrodes 47c from the land inspection region 50b.

At a step ST16, the CPU 46 makes comparison of the land 28c with that of the non-packaged substrate 25 stored in the teaching table 38 with respect to the shape (profile) by referring to the position and shape of the electrode 47c located within the land inspection region, to arithmetically determine (estimate) the portion of the land 28 which is hidden by the part 27c.

Figure 13A:
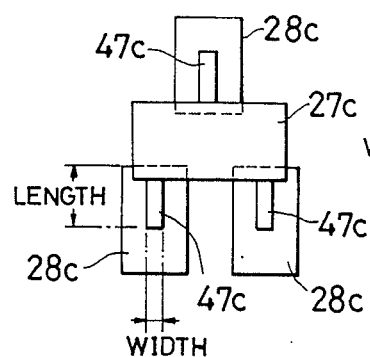
FIG. 13A is a schematic view for illustrating a decision process made on the positional relationship between a transistor or the like part mounted on a substrate and mounting lands therefor.
Figure 13B:
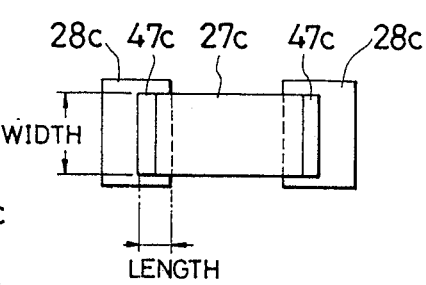
FIG. 13B is a schematic view for illustrating a decision process made on the positional relationship between a resistor or the like part mounted on a substrate and the mounting lands therefor.
Figure 14A:
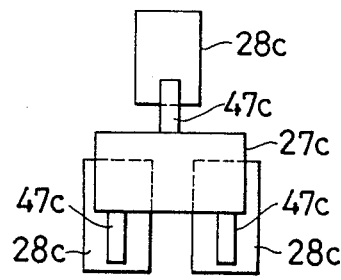
FIGS. 14A, 14B and 14C are schematic views for illustrating, by way of example, possible positional relationships resulting from the decision made for the case shown in FIG. 13A.
Figure 14B:
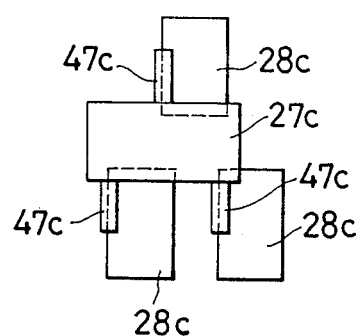
Figure 14C:
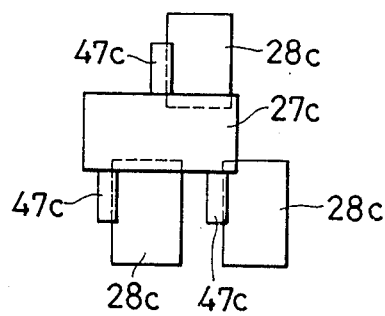

At a step ST17, the CPU 46 utilizes the results of the arithmetic determination to determine the coverage area data (the data of area of the land 28c covered by the part 27c), the width data and the length data which indicate the positional relationship between the land 28c and the part 27c, as shown in FIGS. 13A and 13B. Additionally, it is checked if the values of these data are appropriate.

When the determined data values are found proper, the inspection routine branches from the step ST17 to a step ST18 where it is determined that the part 27c is mounted in a satisfactory manner, which fact is indicated on the CRT display unit 43 and/or printed out by the printer 44.

On the other hand, when it is found at the steps ST13 and ST17 that the feature data of the image located within the inspection region 51b do not coincide with the feature data of the parts 27a stored in the teaching table 38, decision is made that the coverage area data, width data and the length data which are indicative of the positional relationship between the land 28c and the part 27c are not to be satisfactory. In that case, the inspection routine executed by the CPU 46 branches from the steps ST13, ST17 to the step ST19 where the mounting failure, i.e. unsatisfactory mounted state of the part 27c is decided and displayed on the CRT screen 43 and/or printed out by the printer 44.

The abovementioned processing is executed repeatedly for the remaining parts within the first image picked-up area. Upon completion of the inspection processing for all the parts 27c, the inspection routine executed by the CPU 46 returns to a 2nd box of the step ST12 through a step ST20, whereupon execution of the similar processing is repeated for the remaining imaged areas as picked up. Thus, the inspection processing comes to an end at the step 20.

As will be appreciated from the foregoing description, the satisfactory mounted state can be decided so far as the part 27c is mounted on the land 28c within the permissible range even when the land 28c differs from one to another substrate, whereby the erroneous decision attributable to the manufacturing tolerance can be positively prevented. In other words, the permissible positional deviation can thus be automatically established optimally for each of the parts 27c.

Figure 15A:
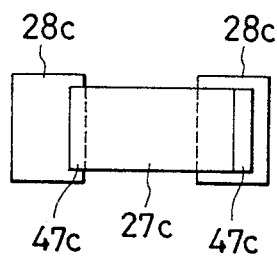
FIGS. 15A, 15B, 15C and 15D are schematic views for illustrating examples of the positional relationship which may result from the decision made for the case shown in FIG. 13B.
Figure 15B:
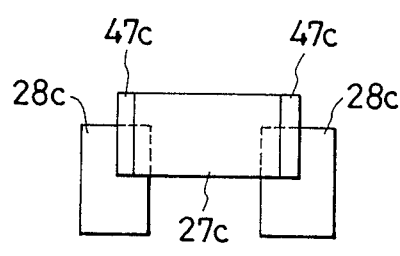
Figure 15C:
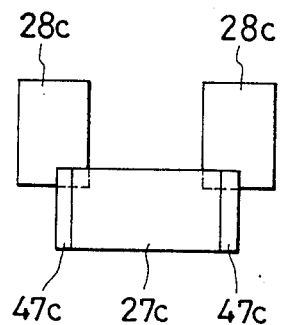
Figure 15D:
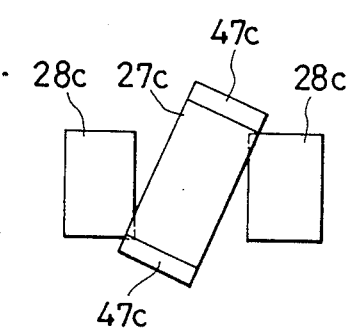

The mounted states of the parts illustrated in FIGS. 14A, 14B, 15A and 15B are decided to be satisfactory, while the mounted states illustrated in FIGS. 15C and 15D are decided to be unsatisfactory.

Although description has been made such that the entry of the species or type data of the part 27a is executed through manual operation of the keyboard, it will be readily understood that the electrodes of the part 27c are detected from the inputted image of the standard packaged substrate and that the species of the part 27a can be automatically determined on the basis of the electrode array to be subsequently loaded internally in the inspection system.

Further, the entry of the feature data of the part 27a assumed to be effected manually can also be realized automatically by making use of the standard packaged substrate.

Figure 16:
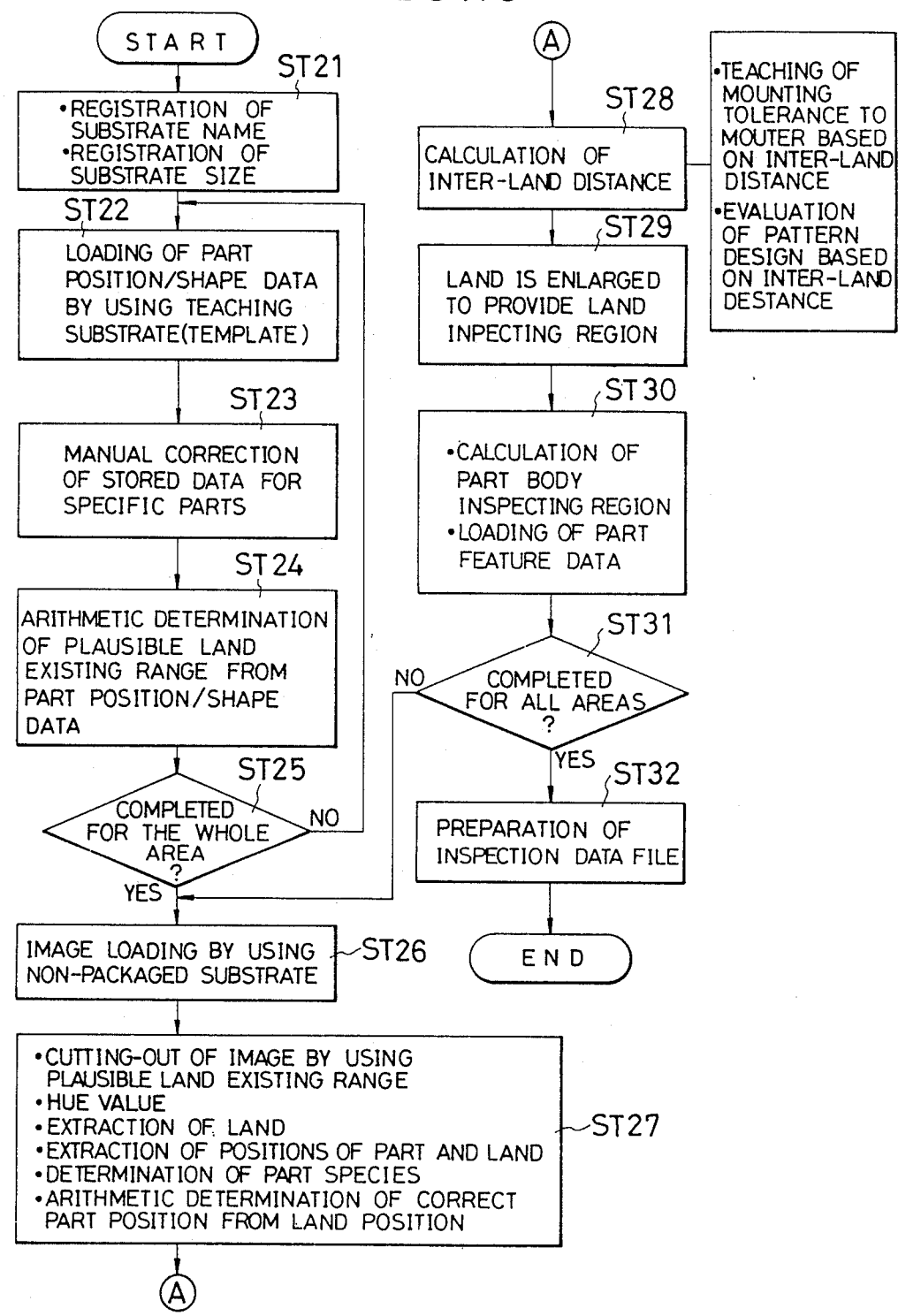
FIG. 16 is a view illustrating in a flow chart a routine for teaching a procedure to discriminatively identify the types or series of parts.
Figure 17:
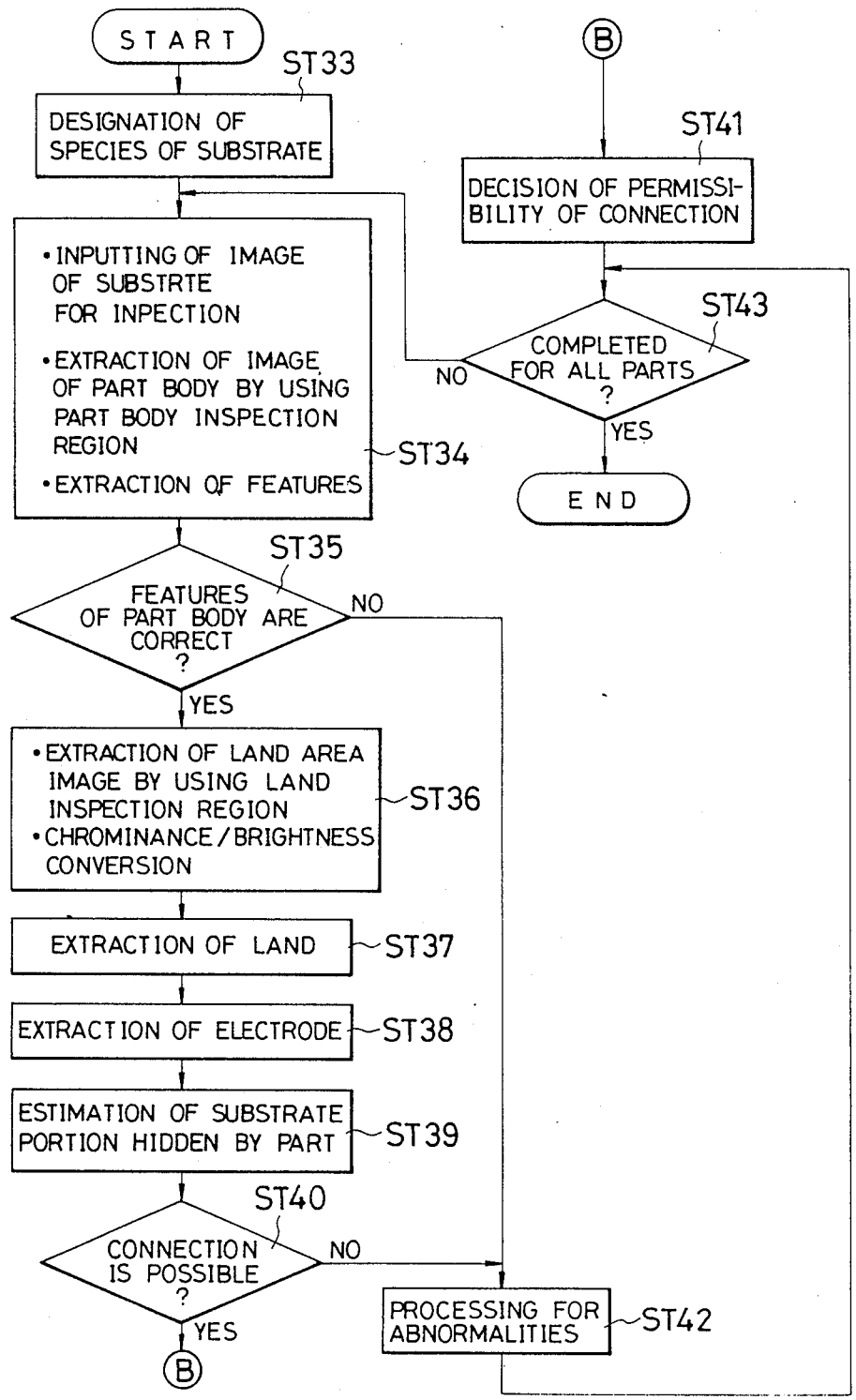
FIG. 17 is a view illustrating in a flow chart an inspecting procedure for identifying disciminatively parts.

FIGS. 16 and 17 are views showing flow charts for illustrating procedures for discriminatively identifying the species of parts mounted on a substrate according to another embodiment of the present invention. The packaged substrate inspecting apparatus adapted for performing this procedure is substantially of the same structure as the one shown in FIG. 4, wherein the land data or information is extracted from the image data obtained by picking up the image of a non-packaged substrate on the basis of position and shape (profile) data of parts inputted by using a substrate prepared for the teaching purpose. Subsequently, the species of the parts are automatically identified on the basis of the land information and the position/shape data mentioned above. A part inspection data file is created for each species of the parts. Inspection of the packaged substrate is performed with reference to the inspection data files.

Now, a procedure for discriminatively identifying the species of electronic/electric parts mounted on a substrate will be described below in detail.

When a new packaged substrate 26 is to be inspected, the CPU 46 commands the CRT display unit 43 to display a message requesting for the entry of data concerning the identification name (e.g. identification number) of the substrate and the size thereof, as illustrated in a teaching flow chart of FIG. 16 at a step ST21.

When the substrate identification name and size data as prompted are entered through the keyboard 45, the CPU 46 waits for disposition of a substrate designed for the teaching purpose on the X-Y table or stage 32 at a step ST22. In this connection, it should be mentioned that the template substrate for the teaching purpose is colored in white at regions where electric/electronic parts are to be mounted with the remaining area being painted in black. When the template substrate 24 has been disposed on the X-Y table assembly 20 through the X-Y stage controller 41 so that a first area of the template substrate 24 whose image is to be picked up is positioned below the color TV camera 34.

The image information produced by the color TV camera 34 undergoes A/D conversion through the A/D converter 36 under the control of the CPU 46. The results of the A/D conversion (i.e. the digitized image data of the substrate 24) is stored in the memory 37 on the real time basis.

Subsequently, the CPU 46 reads out successively the image data of R-pixels (or alternatively, G- or B-pixels) from the memory 37. The image data as read out are then converted into binary signals through the image processor 39, from which the data concerning the white regions on the substrate 24 (the part portion 27a) is extracted. Subsequently, positional data as well as shape (profile) data of the parts 27a obtained through the extracting operation are entered in the teaching table 38.

At a step ST23, the CPU 46 creates a layout image 29 of the parts on the basis of the position data and the shape data of the parts 27a, the layout image being then displayed on the CRT display unit 43, as is shown in FIG. 7. For a specific part, the CPU 46 can produce a message prompting the operator to input manually the relevant data through the keyboard 45.

Subsequently, the CPU 46 reads out sequentially the position data and the shape or profile data of the parts 27a stored in the teaching table 38 at a step ST24, to thereby establish the plausible land covering or existing range 30 for each of the parts 27a, as is illustrated in FIG. 18.

In this connection, it should be mentioned that the plausible land covering range 30 is created for finding out the land to which the part 27a can be connected electrically and mechanically. To this end, the plausible land covering range 30 is given a sufficiently large area so that the land to which the part 27a is to be connected can be extracted regardless of whether the part 27a is a three-electrode element such as transistor or a two-electrode element such as resistor, capacitor or the like.

When the plausible land covering or existing ranges 30 have been established for all the parts, respectively, located within the first imaged area, the CPU 46 places data of the plausible land covering or existing ranges 30 in the teaching table 38. Subsequently, the species identification routine returns to the aforementioned step ST22 by way of a step ST25. When the plausible land existing ranges 30 have been created for all the remaining picked-up areas, the routine jumps from the step ST25 to a step ST26, where the CPU 46 waits for disposition of a non-packaged substrate 25 on the X-Y table assembly 20 after the template substrate 24 for the teaching purpose has been removed therefrom.

When the non-packaged substrate 25 is positioned on the X-Y table 20, the CPU 46 causes the X-Y table 20 to be moved through the X-Y stage controller 451 so that a first area of the non-packaged substrate 25 whose image is to be picked is positioned beneath the color TV camera 34.

Subsequently, the image signal generated by the color TV camera 34 is subjected to A/D conversion under the control of the CPU 46, the result of which (i.e. image data of the non-packaged substrate 25) are stored in the memory 37 on the real time basis.

At a next step 27, the CPU 46 reads out sequentially the data of the plausible land existing range 30 from the teaching table 38 and supplies the data to the image processor unit 39 which is also supplied with the image data of the non-packaged substrate 25 read out from the memory 37. In the image processor unit 39, an image of the plausible land existing range is cut out from the image data mentioned above.

Subsequently, the CPU 46 issues a hue value conversion command to the image processor unit 39 which responds thereto by performing the hue value conversion on individual pixels constituting parts of the image within the plausible land existing range 30. For the hue value conversion, the same conversion equations (1), (2), (3), and (4) as employed in the preceding embodiment are used.

Upon completion of the abovementioned hue value conversion for all the pixels within the plausible land existing range 30, the CPU 46 checks whether the red hue values Rc (i, j) of all the pixels (i, j) within the plausible land existing range 30 exceed a land extracting reference value C (e.g. $C=0.4\cdot\alpha$) which has been previously loaded, for thereby extracting the land 28b located within the plausible land existing range 30.

Subsequently, the position data as well as shape or profile data of the land 28b is stored in the teaching table 38 under the command of the CPU 46, which then verifies the number and the positions of the land 28b which can be connected to the part 27a.

In this conjunction, when there exist three lands 28b capable of being connected to the part 27a as shown in FIG. 19A and when these lands 28a are disposed at opposite sides of the part 27a with a ratio of 1:2, this part 27a is recognized as a transistor by the CPU 46. Thereafter, the CPU 46 determines the correct position of the part 27a for the associated lands 28b to correct the position of the part 27a as is illustrated in FIG. 19B. The corresponding position data of that part 27a stored in the teaching table 38 is also altered correctively on the basis of the result of the conversion mentioned above.

On the other hand, when two lands 28b are present which can be connected to the part 27 and that the lands are provided on opposite ends of the part 27a with a ratio of 1:1, as illustrated in FIG. 20A that part 27a is recognized to be a two-electrode part such as a resistor or capacitor. On the basis of the positions of the lands 28b for the part 27a, the correct position thereof is determined to correct the actual position of the part 27a, as is illustrated in FIG. 20B. The position data of the same part 27a stored in the teaching table 38 is also corrected in accordance with the result of the correction mentioned above.

Subsequently, at a step ST28, the CPU 46 arithmetically determines the inter-land distance among the lands with reference to the parts 27a, respectively. The results (i.e. inter-land distance data) are also stored in the teaching table 33.

It should be mentioned that the inter-land distance data may be utilized for indicating the permissible tolerances of the parts to a mounter for evaluating the land pattern design as shown in a box to the right of step 28.

Next, at a step ST29, the CPU 46 expands or enlarges the shape (profile) of the land 28b, as is illustrated in FIGS. 11A and 11B, to arithmetically determine the land inspecting region 50b, the resulting data of the land inspecting region being stored in the teaching table 38.

Thereafter, at a step ST30, the CPU 46 arithmetically determines a part body inspecting region 51b for the purpose of cutting out the image of a center portion of each part 27a on the basis of the data concerning the position and shape (profile) of the land 28b, as illustrated in FIGS. 12A and 12B, the results also being stored in the teaching table 38. At this stage, a message requesting for the feature data (e.g. color data) of the body of each part 27a is displayed on the CRT display unit. In response, operator enters all the feature data for all the parts 27a manually through the keyboard 45, which are then stored in the teaching table 38 under the control of the CPU 46.

Upon completed execution of the routine including the land extraction processing to the feature data loading processing for all the parts 27a located within the first picked-up area, the CPU 46 returns to the step ST26 by way of a step ST31, whereupon the processing described above is repeatedly executed for all the remaining areas picked-up by the imaging device 34.

When the aforementioned processing comes to an end after having been performed for all the parts in all the picked-up images, the program executed by the CPU 46 jumps to a step ST32 from the step ST31.

At the step ST32, the CUP 46 rearranges the data stored in the teaching table 38 to prepare an inspection data file which is again stored in the teaching table 38, whereupon the teaching operation comes to an end.

When an inspection or identification mode is activated at the end of the teaching operation, the CPU 14 generates a message on the screen of the CRT display unit 43, the message requesting the entry of identification name of a packaged substrate 26 to be inspected at a step ST33 in the inspection flow chart illustrated in FIG. 17.

After the identification name of the substrate has been entered by operator through the keyboard 45, the CPU 46 waits for disposition of a corresponding packaged substrate 26 to be inspected on the X-Y table 32 at a step ST34. When the substrate 26 to be inspected is disposed, the CPU 46 causes the X-Y table assembly 20 to be moved through the X-Y stage controller 41 to the position where the first area to be imaged of the packaged substrate 26 for inspection is located below the color TV camera 34.

The image signal produced by the color TV camera 34 is converted into a digital signal through the A/D converter 36 under the control of the CPU 46, the result of the A/D conversion (i.e. image data of the packaged substrate 26 under test) are stored in the memory 37 on the real time basis.

Subsequently, the CPU 46 reads out the data of a part body inspection region 51b from the teaching table 38 and supplies them to the image processor unit 39 which is also supplied with the image data of the packaged substrate 26 under inspection from the memory 37. In the image processor unit 39, the image of the part body region 51b to be inspected is cut out from the image data.

Next, the CPU 46 issues a feature extracting command to the image processor unit 39 which responds thereto by extracting the feature data of the image of the cut-out part body inspection region 51b (which can be accomplished, for example, through hue value conversion of pixels of the image).

Thereafter, the CPU 46 makes decision at a step ST35 as to whether the feature data of the image located within the aforementioned part body inspection region 51b coincides with the feature data of the parts 27a stored in the teaching table 38. If coincidence is found, the inspection routine makes a jump from the step ST35 to a step ST36 where the land inspection region 50b is read out from the teaching table 38 and transferred to the image processor unit 39 which is also supplied with the image data of the packaged substrate 26 under inspection from the memory 37, whereupon the image of the land inspection region 50b is cut out from that image data.

At this stage, the CPU 46 issues a command for hue value conversion to the image processor unit 39, whereby the individual pixels (picture elements) constituting the aforementioned land inspection region 50b undergo the hue value conversion.

Upon completion of the hue value conversion mentioned above for all the pixels within the land inspection region 50b, the CPU 46 checks whether the red hue value Rc (i, j) for each pixel within the land inspection region 50b exceeds a preset land extraction reference value C (e.g. C may be selected equal to $0.4 \cdot \alpha$), to thereby extract the land 28c located within the land inspection region 50b at a step ST37.

Subsequently, at a step ST38, the CPU 46 checks whether the brightness BRT (i, j) of each pixel within the land inspection region 50b exceeds a preset reference value D for extraction of electrodes, to thereby extracts the electrode images 47c from the land inspection region 50b.

At a step ST39, the CPU 46 makes comparison of the land 28c with that of the land 28b of the non-packaged substrate 25 stored in the teaching table 38 with respect to the shape (profile) by referring to the position and shape of the electrode 47c located within the land inspection region, to thereby arithmetically determine (estimate) the portion of the land 28 which is hidden by the part 27c.

At a step ST40, the CPU 46 utilizes the results of the arithmetic determination to determine the coverage area data (the data of area of the land 28c covered by the part 27c), the width data and the length data which indicate the positional relationship between the land 28c and the part 27c, as is shown in FIGS. 13A and 13B. Additionally, it is checked if the values of these data are appropriate.

When the determined data values are found proper, the inspection routine branches from the step ST40 to a step ST41 where it is determined that the part 27c is mounted in a satisfactory manner, which fact may be indicated on the CRT display unit 43 and/or printed out by the printer 44.

On the other hand, when it is found at the steps ST35 and ST40 that the feature data of the image located within the part body inspection region 51b do not coincide with the feature data of the parts 27a stored in the teaching table 38, decision is made that the coverage area data, width data and the length data which are indicative of the positional relationship between the land 28c and the part 27c are not proper. In that case, the inspection routine executed by the CPU 46 branches from the steps ST35, ST40 to a step ST42 where the mounting failure, i.e. unsatisfactory mounted state of the part 27c, is decided and displayed on the CRT screen 43 and/or printed out by the printer 44 (abnormality processing).

Thereafter, the CPU 46 regains the step ST 34 by way of a step ST 43, whereby the processing described above is executed repeatedly for all the remaining image picked-up areas.

The abovementioned processing is executed repeatedly for the remaining parts located within the first imaged area. Upon completion of the inspection processing for all the parts 27c in all the remaining areas at the step 43, the inspection processing comes to an end.

As will be appreciated from the foregoing description, the manual loading of data in the teaching mode can be significantly simplified with erroneous decision due to erroneous data entry being prevented by virtue of the capability of automatic discriminative identification of the species of parts according to the invention.

Further, the satisfactory mounted state can be decided so far as the part 27c is mounted on the land 28c within the permissible range even when the land 28c differs from one to another substrate, whereby the erroneous decision attributable to the manufacturing tolerance can be positively prevented. In other words, the permissible positional deviation can thus be automatically established optimally for each of the parts 27c.

The mounted states of the parts illustrated in FIGS. 14A, 14B, 15A and 15B are decided to be satisfactory, while the mounted states illustrated in FIGS. 15C and 15D are decided to be unsatisfactory.

Although description has been made such that the entry of the feature data of the part 27a is executed through manual operation of the keyboard 45, it will be readily understood that the entry of the feature data of the part 27a assumed to be effected manually can also be realized automatically by making use of the standard packaged substrate.

Figure 21:
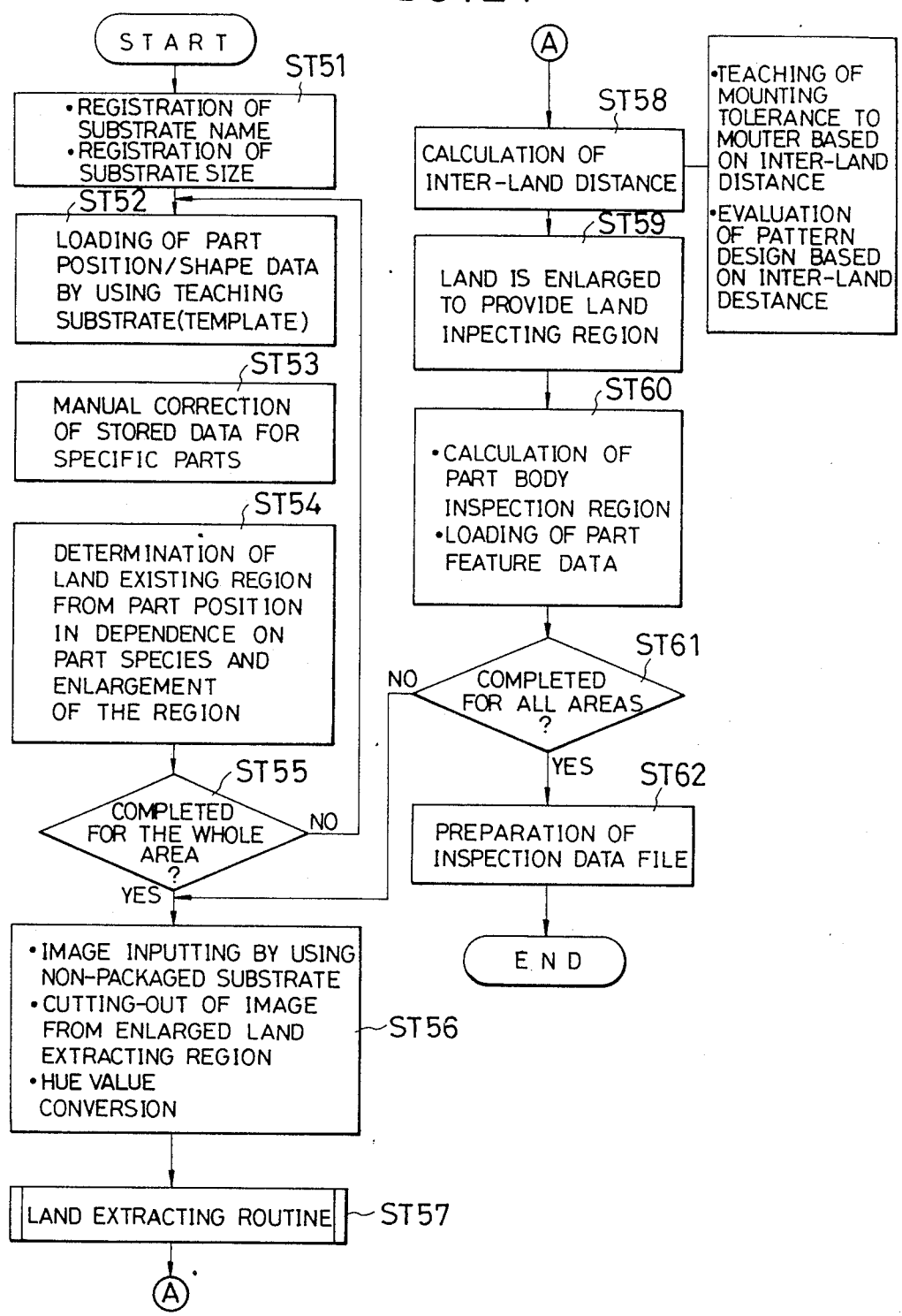
FIG. 21 is a view for illustrating in a flow chart a routine for teaching a pixel (picture element) processing procedure for identifying copper layer or foil deposited on a substrate by the packaged substrate inspecting apparatus shown in FIG. 4.
Figure 22:
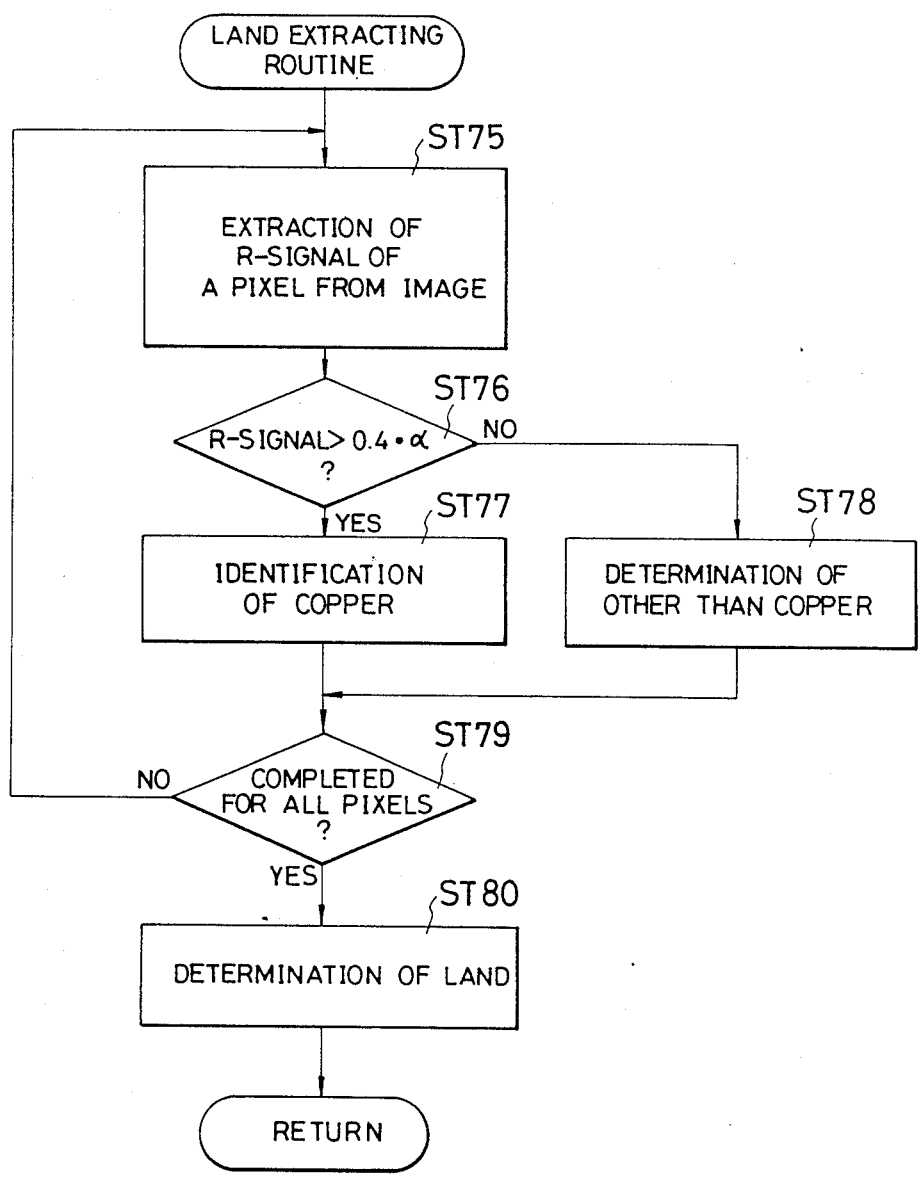
FIG. 22 is a view for illustrating a land extracting routine in the pixel processing procedure for identifying the copper foil or layer on the substrate.
Figure 23:
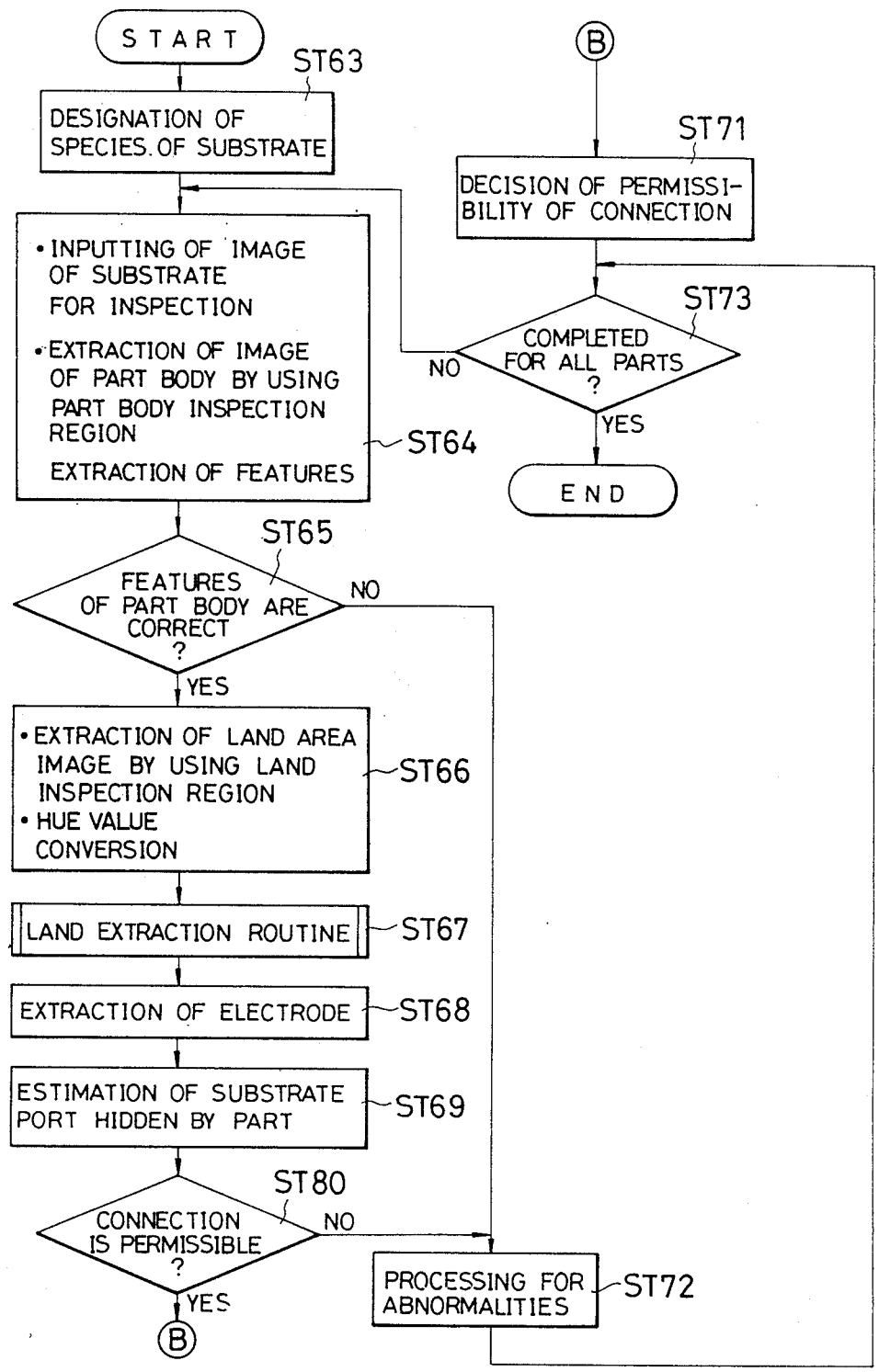
FIG. 23 is a view for illustrating an inspection routine in the pixel identification procedure for the copper layer on the substrate.

FIGS. 21 to 23 are views showing flow charts for illustrating pixel decision procedure for identifying copper layer or foil portions on a substrate according to another embodiment of the present invention.

Describing briefly the operation of the packaged substrate inspection apparatus for executing the copper foil pixel identification, the individual pixels of images obtained by picking up or imaging a non-packaged substrate 25 and a packaged substrate to be tested undergo hue value conversion, wherein when the value of red chrominance signal derived from the pixels exceeds a predetermined value or level, it is decided that the pixels of concern are those of copper foil portion (land portions 28b, 28c). On the basis of the results of this decision, the relative positional relationship between the land 28c and the part 27c is determined, whereby it is decided whether the mounted state of the part 27c is to be satisfied or not.

The copper foil pixel identification procedure is executed by the using the packaged substrate inspecting apparatus shown in FIG. 4 in a manner described below.

FIG. 21 shows a flow chart for illustrating the teaching procedure, in which the processing steps ST51 to ST53 are same as the steps ST21 to ST23 shown in FIG. 16. Accordingly, repeated description of these steps will be unnecessary.

At a step ST54, the CPU 46 generates a message on the CRT display unit 43 prompting the operator to enter information concerning the type or species of the individual parts 27a as well as orientations in which the parts 27a are to be mounted on the substrate. When the information as requested is loaded by the operator, the regions in which the mounting lands are to be positioned (the land extracting regions) are determined on the basis of the data concerning the shape, species and the orientation of the individual parts.

In this connection, it is assumed, by way of example, that the part 27a is a triplet-electrode part such as a transistor. In that case, the land extracting regions 48a which cover electrodes 47a of the part 27a, respectively, and which extend outwardly therefrom is determined, as is illustrated in FIG. 8. On the other hand, in case the part 27a is a double-electrode part such as a resistor, a capacitor or the like, such land extracting regions 48a are prepared which cover the electrodes 47a formed at both ends of the part, respectively, and extend outwardly thereof, as is illustrated in FIG. 9.

Subsequently, the land extracting regions 48b are enlarged, respectively, to create enlarged extracting regions 49a, as is illustrated in FIGS. 10A and 10B for both of the assumed cases mentioned above. The data of the enlarged land extracting regions 49a are then stored in the teaching table 38.

Thereafter, the abovementioned processing is executed for other parts to be mounted in the first picked-up area.

When the processing for preparing the land extracting regions 49a for all the parts 27a to be disposed within the first area has been completed, the routine returns to the step ST52 by way of a step ST55, being followed by repeated execution of the abovementioned processing for all of the remaining image picked-up areas. When the requisite data of the land extracting regions 49a for all the parts 27a belonging to every picked-up area has been obtained, the routine makes a jump to a step ST56 from the step ST55.

At the step ST56, the CPU 46 waits for the positioning of a non-packaged substrate 25 on the X-Y table or stage 20 after the template substrate for the teaching routine is removed.

When the non-packaged substrate 25 is positioned on the X-Y table 20, the CPU 46 causes the X-Y table 20 to be moved through the X-Y stage controller 41 so that a first area of the non-packaged substrate 25 whose image is to be picked is positioned beneath the color TV camera 34.

Subsequently, the image signal generated by the color TV camera 34 is subjected to A/D conversion under the control of the CPU 46, the result of which (i.e. image data of the non-packaged substrate 25) are stored in the memory 37 on the real time basis.

Next, the CPU 46 reads out the data of the enlarged land extracting regions 49a from the teaching table 38 and supplies the data to the image processor unit 39 which is also supplied with the image data of the non-packaged substrate 25 read out from the memory 37. In the image processor unit 39, an image (referred to as intra-land image) is cut out from the data of each land extracting region 49a.

Subsequently, the CPU 46 issues a hue value conversion command to the image processor unit 39 which responds thereto by performing the hue value conversion on pixels constituting parts of the intra-land image in accordance with hue value conversion equations described hereinbefore in conjunction with the first embodiment of the invention.

Upon completion of the abovementioned hue value conversion for all the pixels (picture elements) within the land extracting regions 49a, the CPU 46 calls a land extracting routine illustrated in FIG. 22 at a step ST57. In this routine, the red hue value Rc (i, j) for one pixel (i, j) is extracted at a step ST75. Subsequently, the CPU 46 checks at a step ST76 whether the red hue value Rc (i, j) exceeds a preset land extraction reference value C (e.g. C may be selected equal to 0.4·α), to thereby decide that the pixel (i, j) corresponding to the abovementioned red hue value Rc (i, j) is that of the copper foil or layer at a step ST77, if Rc (i, j) is greater than C. On the other hand, when Rc (i, j) is smaller than or equal to C, the CPU 46 decides that the pixel (i, j) corresponding to the above hue value Rc (i, j) is that of other region than the copper layer at a step ST78. CPU 46 returns to the step ST75 from the step ST79, if the copper/non-copper foil decision processing for all pixels has not been completed.

Upon completion of the copper/non-copper foil decision processing for all the pixels within the land extracting region 49a, the routine executed by the CPU 46 branches to a step ST80 by way of a step ST79 where the position data and the profile (shape) data of the land 28b are arithmetically determined (i.e. extracted) on the basis of the data representing the pixels decided to belong to the coil layer portion. Thereafter, the main routine is regained.

The position data as well as shape or profile data of the land 28b is stored in the teaching table 38 under the command of the CPU 46 at a step ST58. At the same time, the CPU 46 arithmetically determines the distance among the lands destined for mounting the individual parts 27a, respectively, the results of which are also stored in the teaching table 38 as the distance data.

It should be mentioned that the distance data may be utilized for indicating the permissible tolerances involved in mounting the parts to the part mounting mechanism referred to as the mounter for evaluating the design of land pattern as shown in a box to the right of step 58.

At a next step ST59, the CPU 46 expands or enlarges the shape (profile) data of the land 28b, as is illustrated in FIGS. 11A and 11B, to arithmetically determine the land inspecting region 50b, the resulting data being stored in the teaching table 38.

Thereafter, at a step ST60, the CPU 46 arithmetically determines a part body inspecting region 51b for cutting out the image of a center portion of each part 27a on the basis of the data concerning the position and shape (profile) of the land 28b, as illustrated in FIGS. 12A and 12B, the results also being stored in the teaching table 38. At this stage, a message prompting the entry of the feature data (e.g. color data) of the body of each part 27a is displayed on the CRT display unit 43. In response, operator enters all the feature data for all the parts 27a manually through the keyboard 45, which are then stored in the teaching table 38.

Then, the routine returns to the step ST56 by way of a step ST61 where the subroutine involved between the land extracting step and the feature data input step, inclusive thereof, is executed repeatedly for the remaining picked-up areas.

When the abovementioned processing has been completed for the parts 27a existing in all the picked-up areas, execution of the CPU jumps to a step ST62 from the step ST61.

At the step ST62, the CPU 46 rearranges the data stored in the teaching table 38 to prepare an inspection data file which is again stored in the teaching table 38, whereupon the teaching operation comes to an end.

When an inspection mode is activated at the end of the teaching operation, the CPU 46 generates a message on the screen of the CRT display unit 43, the message requesting for the loading of identification name of a packaged substrate 26 to be inspected at a step ST63 in the inspection flow chart illustrated in FIG. 23.

After the identification name of the substrate has been entered by operator through the keyboard 45, the CPU 46 waits for disposition of a corresponding packaged substrate 26 to be inspected on the X-Y table 32 at a step ST64. When the substrate 26 to be inspected is disposed, the CPU 46 causes the X-Y table 20 to be moved through the X-Y stage controller 41 to the position where the first area to be imaged of the packaged substrate for inspection is positioned below the color TV camera 34.

The image signal produced by the color TV camera 34 is converted into a digital signal through the A/D converter 36 under the control of the CPU 46, the result of the A/D conversion (i.e. image data of the packaged substrate 26 under test) are stored in the memory 37 on the real time basis.

Subsequently, the CPU 46 reads out the data of part body inspection region 51b from the teaching table 38 and transmits them to the image processor unit 39 which is also supplied with the image data of the packaged substrate 26 under test from the memory 37. In the image processor unit 39, the image of the region 51b to be inspected is cut out from the image data.

Next, the CPU 46 issues a feature extracting command to the image processor unit 39 which responds thereto by extracting the feature data of the cut-out image of the part body inspection region 51b (which can be accomplished, for example, through hue value conversion of pixels of the image).

Thereafter, the CPU 46 makes decision at a step ST65 as to whether the feature data of the image within the aforementioned part body inspection region 51b coincides with the feature data of the parts 27a stored in the teaching table 38. If coincidence is found, the inspection routine makes a jump from the step ST65 to a step ST66 where the land inspection region 50b is read out from the teaching table 38 and transferred to the image processor unit 39 which is also supplied with the image data of the packaged substrate 26 under inspection from the memory 37, whereupon the image of the land inspection region 50b is cut out from that image data.

At this stage, the CPU 46 issues a command for hue value conversion to the image processor unit 39, whereby the individual pixels (picture elements) constituting the aforementioned land inspection region 50b undergo the hue value conversion.

Upon completion of the hue value conversion mentioned above for all the pixels within the land inspection region 50b, the CPU 46 checks at a step ST67 whether the red hue value Rc (i, j) for the pixel (i, j) within the land inspection region 50b exceeds a preset land extraction reference value (e.g. C=0.4·α), to thereby extract the land 28c located within the land inspection region 50b.

Subsequently, the CPU 46 checks whether the brightness BRT (i, j) of each pixel within the land inspection region 50b exceeds a preset reference value D for extraction of electrodes, to thereby extracts the electrodes 47c from the land inspection region 50b at a step ST68.

At a step ST69, the CPU 46 makes comparison of the land 28c with that of the non-packaged substrate 25 stored in the teaching table 38 with respect to the shape (profile) by referring to the position and shape of the electrode 47c located within the land inspection region 50b, to arithmetically determine (estimate) the portion of the land 28c which is hidden by the part 27c.

At a step ST70, the CPU 46 utilizes the results of the arithmetic determination to determine the coverage area data (the data of area of the land 28c covered by the part 27c), the width data and the length data which indicate the positional relationship between the land 28c and the part 27c, as shown in FIGS. 13A and 13B. Additionally, it is checked if the values of these data are appropriate.

When the determined data values are found proper, the routine branches from the step ST70 to a step ST71 where it is determined that the part 27c is mounted in a satisfactory manner, which fact in turn is indicated on the CRT display unit 43 and/or printed out by the printer 44.

On the other hand, when it is found a the steps ST65 and ST70 that the feature data of the image located within the inspection region 51b do not coincide with the feature data of the parts 27a stored in the teaching table 38, decision is made that the coverage area data, width data and the length data which are indicative of the positional relation between the land 28c and the part 27c are improper. In that case, the inspection routine executed by the CPU 46 branches from the steps ST65, ST70 to the step ST72 where the mounting failure (i.e. unsatisfactory mounted state of the part 27c) is decided and displayed on the CRT screen 43 and/or printed out by the printer 44.

Upon completion of the inspection processing for all the parts 27c, the inspection routine executed by the CPU 46 returns to the step ST64 through a step ST73, whereupon execution of the similar processing is repeated for the remaining imaged areas as picked up. Thus, at the step 73 the inspection processing comes to an end.

As will be appreciated from the foregoing description, it is possible to extract the lands 28b and 28c according to the embodiment of the invention mentioned just above, wherein it is decided that the mounted state is to be satisfactory so far as the parts 27c lies within the permissible range on the land 28c even when the land 28c of the packaged substrate 26 under test differs from one to another substrate. Besides, the erroneous decision attributable to the manufacturing tolerance can be positively prevented. In other words, the permissible positional deviation can be automatically established optimally for each of the parts 27c.

The mounted states of the parts illustrated in FIGS. 14A, 14B, 15A and 15B are decided to be satisfactory, while the mounted states illustrated in FIGS. 15C and 15D are decided to be unsatisfactory.

Although description has been made such that the entry of the species or type data of the part 27a is executed through manual operation of the keyboard, it will be readily understood that the electrodes of the part 27c may be detected from the inputted image of the standard packaged substrate and that the species of the part 27a can be automatically determined on the basis of the electrode array to be subsequently loaded internally in the inspection system.

Although it has been assumed in the foregoing description that the hue value conversion of the image is carried out by the image processing unit 39, it is to be understood that the output of the imaging device may also be subjected to analogue processing. Further, the hue value conversion may be realized with the aid of program or software in the CPU 46.

The manual inputting of the feature data of the part 27a in the teaching mode may be readily replaced by automatic inputting procedure by using a reference or standard package substrate.

Although the invention has been described in conjunction with the preferred and exemplary embodiments, it should be understood that many and various modifications in details will readily occur to those skilled in the art without departing from the spirit and scope of the invention set forth in claims.

I claim:

1. A component-mounted printed circuit board inspecting apparatus, comprising:
   image taking means for producing images of a bare printed circuit board and a component-mounted printed circuit board;
   land extracting means for extracting conductor lands on which components are to be mounted from said images produced by the image taking means and for obtaining geometrical data of the conductor lands;
   positional relation determining means for determining positional relationships between the lands of the component-mounted board and components mounted thereon on the basis of said geometrical data obtained by the land extracting means; and
   decision means for deciding if placement of a component is proper based on said positional relationships obtained by the positional relation determining means.

2. A component-mounted printed circuit board inspecting apparatus according to claim 1, wherein said geometrical data obtained by said land extracting means is subjected to hue value conversion for the conductor lands.

3. A component-mounted printed circuit board inspecting apparatus, comprising:
   imaging means for taking first images of a printed circuit board;
   image extracting means for extracting second images within a plausible land existing area from said first images of a printed circuit board on the basis of previously inputted data concerning location and geometrical configuration of a component;
   land extracting means for extracting a land image from said second image; and
   decision means for deciding if placement of a component is proper based on said land image and said previously inputted data concerning the location and geometrical configuration of said component.

4. A component-mounted printed circuit board inspecting apparatus according to claim 3, further including display means for displaying the result of a decision of proper or improper placement of a component.

5. A component-mounted printed circuit board inspecting apparatus according to claim 3, further including printer means for printing the result of a decision of proper or improper placement of a component.

* * * * *